United States Patent
Haarala et al.

(10) Patent No.: US 10,589,065 B2
(45) Date of Patent: *Mar. 17, 2020

(54) CATHETER ASSEMBLY INCLUDING SEALING MEMBER

(71) Applicant: Covidien LP, Mansfield, MA (US)

(72) Inventors: Brett Haarala, Framingham, MA (US); Richard M. Braga, North Easton, MA (US)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/055,198

(22) Filed: Aug. 6, 2018

(65) Prior Publication Data

US 2018/0344976 A1 Dec. 6, 2018

Related U.S. Application Data

(63) Continuation of application No. 12/894,249, filed on Sep. 30, 2010, now Pat. No. 10,166,365.

(51) Int. Cl.
*A61M 25/00* (2006.01)
*A61M 39/10* (2006.01)
*A61M 25/18* (2006.01)

(52) U.S. Cl.
CPC .... *A61M 25/0097* (2013.01); *A61M 25/0028* (2013.01); *A61M 25/0014* (2013.01); *A61M 39/10* (2013.01); *A61M 2025/0031* (2013.01); *A61M 2025/0037* (2013.01)

(58) Field of Classification Search
CPC .......... A61M 25/0097; A61M 25/0028; A61M 25/0014; A61M 39/10; A61M 2025/0037; A61M 2025/0031
See application file for complete search history.

(56) References Cited

U.S. PATENT DOCUMENTS

| 4,214,779 A | 7/1980 | Losell |
| 4,674,496 A | 6/1987 | Svadjian et al. |
| 5,059,170 A | 10/1991 | Cameron |

(Continued)

FOREIGN PATENT DOCUMENTS

| WO | 2003000116 A2 | 1/2003 |
| WO | 03/033049 | 4/2003 |

(Continued)

OTHER PUBLICATIONS

"Hydrogels". Society for Biomaterials. Dated Jun. 1, 2007. [Online] http://biomaterials-org.securec7.ezhostingserver.com/week/bio17.cfm. Accessed on Aug. 1, 2019. (Year: 2007).*

(Continued)

*Primary Examiner* — Jenna Zhang
(74) *Attorney, Agent, or Firm* — Kenneth Collier; Jessica Kwak Rauckman

(57) ABSTRACT

A catheter assembly includes a catheter, a hub, and a sealing member. The catheter defines one or more lumens. The hub includes one or more hub extensions dimensioned to be received within the one or more lumens of the catheter. The sealing member is positioned adjacent the interface of the catheter and the hub. The sealing member includes an expandable material which increases in volume upon exposure to moisture.

20 Claims, 3 Drawing Sheets

(56) References Cited

U.S. PATENT DOCUMENTS

| | | |
|---|---|---|
| 5,129,891 A | 7/1992 | Young |
| 5,279,597 A | 1/1994 | Dassa et al. |
| 5,401,245 A | 3/1995 | Haining |
| 5,505,714 A | 4/1996 | Dassa et al. |
| 5,636,875 A | 6/1997 | Wasser |
| 6,099,519 A | 8/2000 | Olsen et al. |
| 6,113,572 A | 9/2000 | Galley et al. |
| 6,423,053 B1 | 7/2002 | Lee |
| 6,638,242 B2 | 10/2003 | Wilson et al. |
| 6,872,198 B1 | 3/2005 | Wilson et al. |
| 6,916,051 B2 | 7/2005 | Fisher |
| 6,921,396 B1 | 7/2005 | Wilson et al. |
| 6,969,381 B2 | 11/2005 | Voorhees |
| 7,163,531 B2 | 1/2007 | Seese et al. |
| 7,300,430 B2 | 11/2007 | Wilson et al. |
| 7,310,544 B2 | 12/2007 | Brister et al. |
| 7,377,915 B2 | 5/2008 | Rasmussen et al. |
| 10,166,365 B2 * | 1/2019 | Haarala .............. A61M 25/0097 |
| 2003/0023190 A1 * | 1/2003 | Cox ...................... A61L 29/085 600/585 |
| 2003/0153898 A1 * | 8/2003 | Schon ............... A61M 25/0009 604/544 |
| 2004/0065333 A1 | 4/2004 | Wilson et al. |
| 2004/0167478 A1 | 8/2004 | Mooney et al. |
| 2005/0107770 A1 | 5/2005 | Schweikert et al. |
| 2005/0261665 A1 | 11/2005 | Voorhees |
| 2005/0267400 A1 | 12/2005 | Haarala et al. |
| 2006/0015086 A1 | 1/2006 | Rasmussen et al. |
| 2006/0189961 A1 * | 8/2006 | Miyahara .............. A61M 39/14 604/535 |
| 2006/0276773 A1 * | 12/2006 | Wilson ............... A61M 25/0097 604/523 |
| 2007/0016167 A1 | 1/2007 | Smith et al. |
| 2007/0060866 A1 | 3/2007 | Raulerson et al. |
| 2007/0196414 A1 * | 8/2007 | Hammarsten ..... A61M 25/0097 424/422 |
| 2008/0147012 A1 * | 6/2008 | Rome ................ A61M 25/0075 604/167.04 |
| 2008/0214991 A1 * | 9/2008 | Haarala .............. A61M 25/0097 604/43 |
| 2009/0054845 A1 * | 2/2009 | Puhasmagi .............. A61L 29/06 604/180 |
| 2010/0010445 A1 * | 1/2010 | Powers ............. A61M 25/0014 604/164.03 |
| 2010/0137778 A1 * | 6/2010 | Kunjan .............. A61B 5/14535 604/6.15 |
| 2010/0204635 A1 | 8/2010 | Haarala et al. |
| 2012/0083750 A1 * | 4/2012 | Sansoucy ............ A61M 39/162 604/265 |

FOREIGN PATENT DOCUMENTS

| | | |
|---|---|---|
| WO | 2004/108183 | 12/2004 |
| WO | 2009/129352 | 10/2009 |

OTHER PUBLICATIONS

Third Office Action issued in Chinese Application No. 201110348244.5 dated Jun. 27, 2014.

European Examination Report from Application No. EP 11183053.5 dated Jun. 13, 2014.

First Office Action issued in the corresponding Chinese Application No. 201110348244.5 dated Apr. 15, 2013.

Extended Search Report from counterpart European Application No. 11183053.5, dated Nov. 28, 2011; 6 pages.

Second Office Action and English translation thereof, from counterpart Chinese Application No. 201110348244.5, dated Dec. 10, 2013, 10 pp.

Examination Report from counterpart European Application No. 11183053.5, dated Jul. 19, 2013, 5 pp.

Text Intended to Grant from counterpart European Application No. 11183053.5, dated Sep. 7, 2015, 19 pp.

Response to Examination Report dated Jun. 13, 2014, from counterpart European Application No. 11183053.5, filed Sep. 11, 2014, 9 pp.

Response to Examination Report dated Jul. 19, 2013, from counterpart European Application No. 111830535, filed Nov. 5, 2013, 10 pp.

Response to Extended European Search Report dated Nov. 28, 2011, from counterpart European Application No. 11183053.5, filed Sep. 28, 2012, 10 pp.

Prosecution History from U.S. Appl. No. 12/894,249, dated Jul. 20, 2012 through Jun. 26, 2018, 204 pp.

* cited by examiner

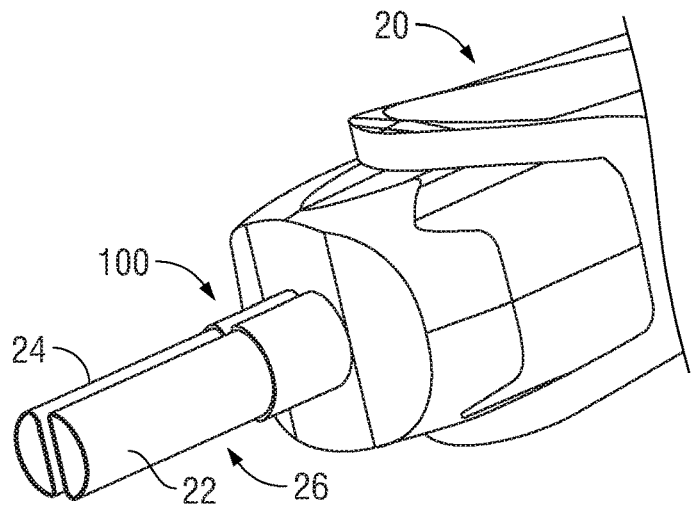
FIG. 2
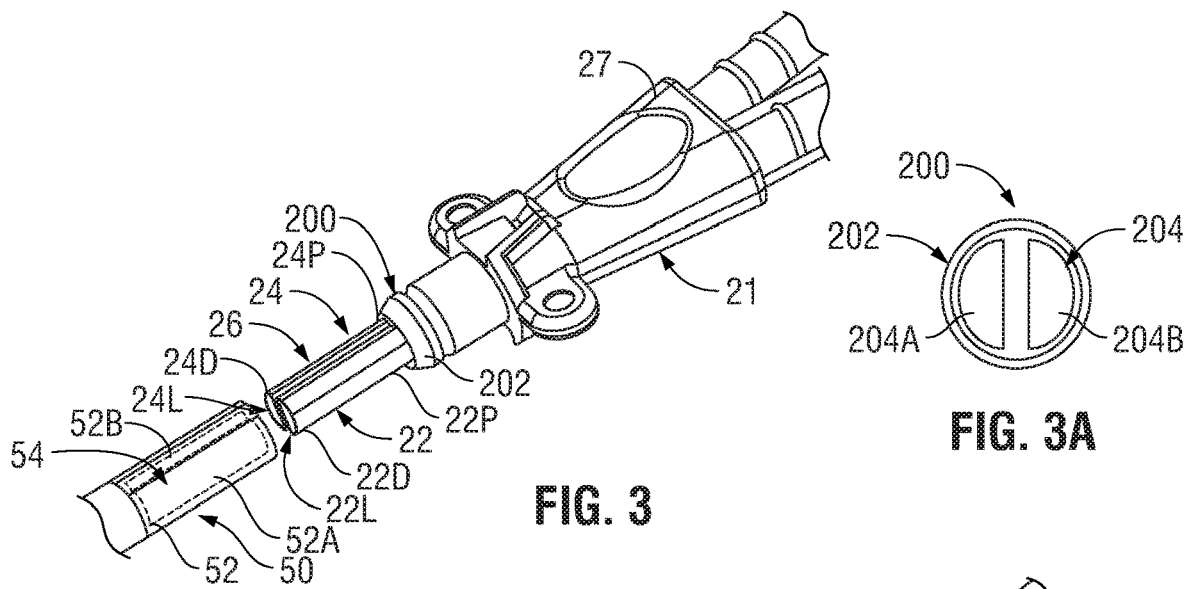
FIG. 3
FIG. 3A
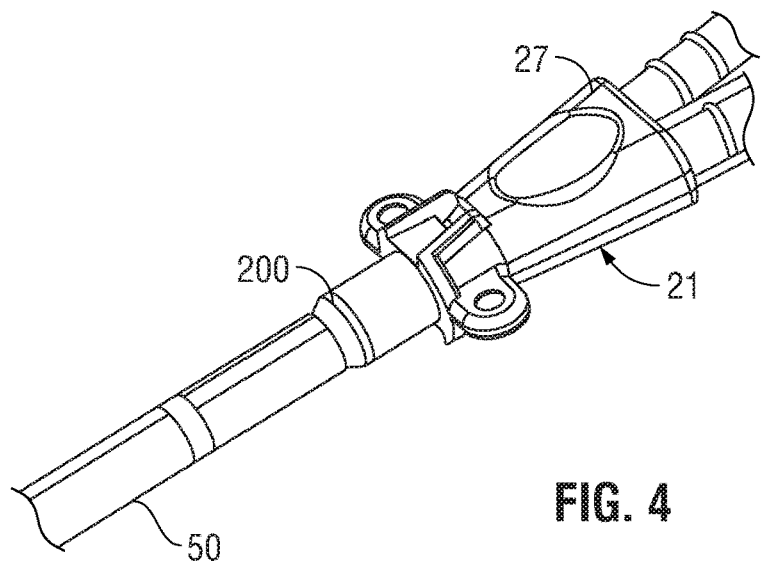
FIG. 4

CATHETER ASSEMBLY INCLUDING SEALING MEMBER

CROSS-REFERENCE TO RELATED APPLICATION

This application is a continuation of U.S. patent application Ser. No. 12/894,249, filed on Sep. 30, 2010, the entire content of which is hereby incorporated by reference.

BACKGROUND

Technical Field

The present disclosure generally relates to catheter assemblies. More particularly, the present disclosure relates to a catheter assembly including one or more sealing members for facilitating the fluid interconnection between two or more surfaces of the catheter assembly.

Description of the Related Art

Catheters are flexible medical instruments which facilitate the withdrawal and introduction of fluids from and to body cavities, ducts, and vessels. Catheters may have particular application in a hemodialysis procedure where blood is withdrawn from a blood vessel for treatment, and subsequently returned to the blood vessel for circulation. Known hemodialysis catheter assemblies include multiple lumen catheters, such as dual lumen or triple-lumen catheters, which permit bi-directional fluid flow within the catheter whereby one lumen is dedicated for withdrawal of blood from a vessel and the other lumen is dedicated for return of treated blood to the vessel. During an exemplary hemodialysis procedure, a multiple lumen catheter is inserted into a body and blood is withdrawn through an arterial lumen of the catheter. The removed blood is directed to a hemodialysis machine, via extension tubes, which dialyzes, or purifies, the blood to remove waste and toxins. The dialyzed blood is returned to the patient through a venous lumen of the catheter. One example of such a catheter is described in U.S. patent application Ser. No. 12/041,563 filed on Mar. 3, 2008, now U.S. Pat. No. 7,731,708, the entire contents of which are incorporated herein by this reference.

Typically, a multiple lumen catheter assembly includes a flexible multiple lumen catheter which is connected to a distal side of a more rigid hub assembly and an extension tube assembly which is connected to a proximal side of the hub assembly and is adapted to communicate with a medical device, such as a hemodialysis machine. The connection between the hub assembly and the catheter lumens may be effected by providing a close geometric fit between lumens of the catheter and hub extensions. Such a tight geometric fit may not always provide a fluid tight seal.

Consequently, it would be desirable to provide an improved seal between the rigid hub assembly and catheter of a catheter assembly as well as between other interconnected components of medical devices.

SUMMARY

In general, in one aspect of the present disclosure, a catheter assembly includes a catheter, a hub, and a sealing member. At least a portion of one or both of the catheter and the hub may include a rigid material and at least a portion of one or both of the catheter and the hub may include an elastomeric material. The catheter defines one or more lumens. The hub includes one or more hub extensions dimensioned to be received within the one or more lumens of the catheter. The hub may further include a casing. The casing defines a cavity configured and dimensioned to accommodate the sealing member. The sealing member is positioned adjacent the interface of the catheter and the hub. The sealing member may include a bioactive agent. The sealing member includes an expandable material which increases in volume upon exposure to moisture. The expandable material may expand to a volume sized to improve the seal at the interface. The expandable material may include a hydrophilic polymer and/or a hydrophilic gel.

The one or more hub extensions define a first connector surface and the catheter defines a second connector surface. The first and second connector surfaces form a tight geometric fit when the one or more hub extensions are received within the one or more lumens of the catheter. The sealing member may be coated on at least a portion of one or both of the first and second connector surfaces.

In embodiments, the sealing member may define a sleeve. The sleeve is positionable on at least a portion of one or both of the first and second connection surfaces. One or more of the catheter, the one or more hub extensions, and the sleeve may define two or more lumens. The sleeve is dimensioned to accommodate one or more of the two or more lumens of one or both of the catheter and the one or more hub extensions. One or more of the lumens of the catheter, the one or more hub extensions, and the sleeve may be substantially D-shaped.

BRIEF DESCRIPTION OF THE DRAWINGS

Various embodiments of the presently disclosed catheter assemblies including improved sealing features are described herein with references to the accompanying drawings, wherein:

FIG. 2 is an enlarged perspective view of a distal portion of the hub assembly of the catheter assembly shown in FIG. 1 with one embodiment of the presently disclosed sealing member positioned thereon;

FIG. 3 is a perspective view, with parts separated, of a portion of another embodiment of a catheter assembly according to the present disclosure;

FIG. 3A is a front plan view of the sealing member of FIG. 3;

FIG. 4 is a perspective view of the catheter assembly of FIG. 3 after the hub assembly and catheter have been assembled.

DETAILED DESCRIPTION OF THE EMBODIMENTS

In the discussion that follows, the term "proximal" or "trailing" will refer to the portion of a structure that is closer to a clinician, while the term "distal" or "leading" will refer to the portion of a structure that is farther from the clinician. As used herein, the term "subject" refers to a human patient or other animal. The term "clinician" refers to a doctor, nurse or other care provider and may include support personnel.

Figure 1:
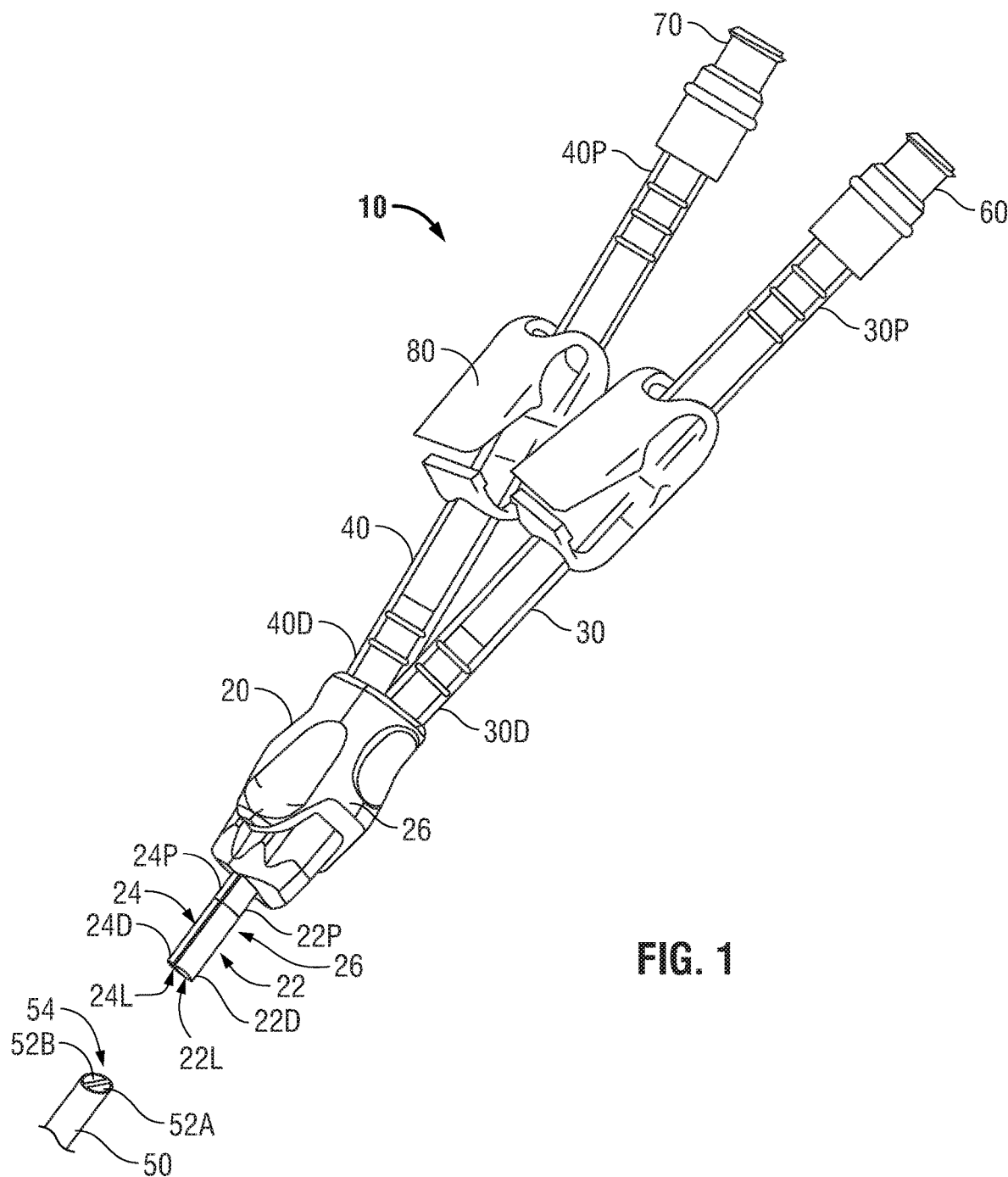
FIG. 1 is a perspective view of a catheter assembly in accordance with the present disclosure.

FIG. 1 illustrates one embodiment of a catheter assembly 10. The catheter assembly 10 includes a catheter 50, a hub assembly 20 and first and second extension tubes 30, 40 extending proximally from the hub assembly 20. The hub assembly 20 includes a hub 26 and one or more hub extensions 22, 24 which extend distally from the hub 26. The hub extensions 22, 24 each define substantially D-shaped lumens 22L, 24L therethrough. In particular, hub extensions 22, 24 each have a proximal end 22P, 24P and a distal end 22D, 24D. At least a portion of the hub assembly 20 may include a substantially rigid material, such as a polymeric material.

The catheter 50 defines one or more lumens. In embodiments, the catheter 50 defines two adjacent substantially D-shaped lumens 52A, 52B. The lumens 52A, 52B of the catheter 50 have complimentary mating surfaces with the D-shaped hub extensions 22, 24. As illustrated, distal ends 22D, 24D of the hub extensions 22, 24 may be positioned within lumens 52A, 52B of catheter 50. The one or more hub extensions 22, 24 are dimensioned to be received within the one or more lumens 52A, 52B of the catheter 50 and define one or more first connector surfaces 26. The catheter 50 defines one or more second connector surfaces 54 that engage first connector surfaces 26 in a close geometric fit when the one or more hub extensions 22, 24 are received within the one or more lumens 52A, 52B of the catheter 50. In this manner, hub assembly 20 fluidly couples first and second extension tubes 30, 40 with catheter 50. Alternately, the catheter lumens and hub extensions may have a variety of different configurations.

With continued reference to FIG. 1, the first extension tube 30 has a proximal end 30P and a distal end 30D. Distal end 30D of first extension tube 30 is attached to hub assembly 20 and proximal end 30P of first extension tube 30 is connected to a first luer adapter 60. Second extension tube 40 has a proximal end 40P and a distal end 40D. Distal end 40D of second extension tube 40 is coupled to hub assembly 20, while proximal end 40P of second extension tube 40 is coupled to a second luer adapter 70. Each extension tube 30, 40 may include a clamp 80 for inhibiting and/or permitting the passage of fluids through extension tubes 30, 40 upon the clamping and/or unclamping thereof.

Referring now to FIG. 2, hub extensions 22, 24 of hub assembly 20 may include a sealing member 100 positioned thereon in order to provide a close geometric compression fit seal at the interface between the hub assembly 20 and the catheter 50. The sealing member 100 is positioned adjacent the interface of the catheter 50 and the hub assembly 20 and is formed of an expandable material which increases in volume upon exposure to moisture, such as blood. The expandable material may expand to a volume sized to improve the seal at the interface of the catheter 50 and the hub 26. In this respect, the expandable material fills any gaps at the interface upon exposure to moisture to prevent the ingression and/or egression of fluids between catheter 50 and hub extensions 22, 24 of hub assembly 20. The expandable material may include a hydrophilic polymer, such as Tecophilic®, and/or a hydrophilic gel. During and/or after assembly, the expandable material may be exposed to water to cause the expandable material to expand to help seal the catheter 50 to the hub 26, and lessen or eliminate any potential leaks. The sealing member 100 may also include any suitable bioactive agent to prevent undesirable biological growth.

The sealing member 100 may be coated and/or chemically bonded to the external surface of at least a portion of the hub extensions 22, 24 relative to the one or more first connector surfaces 26. As illustrated in FIG. 2, the sealing member 100 is coated on the proximal ends 22P, 24P of the hub extensions 22, 24. Alternately, the sealing member 100 may be coated and/or chemically bonded to at least a portion of the inner wall of catheter 50 defining the one or more lumens 52A, 52B of the catheter 50. In this respect, the sealing member 100 may improve the securement of the catheter 50 to the hub assembly 20 and may improve the seal between the catheter 50 and hub assembly 20.

With reference to FIGS. 3-4, in another embodiment, a sealing member, generally referred to as 200, is provided which is similar to sealing member 100. However, as best illustrated in FIG. 3A, sealing member 200 defines a sleeve 202. In embodiments, the sleeve 202 may define a gasket (e.g., an o-ring) type seal. The sleeve 202 is positionable relative to at least a portion of one or more of the first and second connection surfaces 26, 54. The sleeve 202 may be produced by a coating applied to a portion of the hub assembly 20 in liquid suspension that dries to form the sleeve 202.

As shown in FIG. 3A, the sleeve 202 defines one or more lumens 204A, 204B dimensioned to accommodate the hub extensions 22, 24 of hub assembly 20. In the illustrated embodiment, the sleeve 202 defines two adjacent substantially D-shaped lumens 204A, 204B that are dimensioned to receive hub extensions 22, 24 of hub assembly 21. When catheter 50 is secured to hub extensions 22, 24 of hub assembly 21, sealing member 200 is compressed between a body 27 of hub assembly 21 and a proximal end of catheter 50 (FIG. 4). As discussed above with respect to sealing member 100, sealing member 200 is formed from an expandable material, such as a hydrophilic polymer, which expands upon exposure to moisture to improve the seal between the catheter 50 and the hub extensions 22, 24 of hub assembly 21. Because the sealing member 200 is compressed between a body 27 of hub assembly 21 and the proximal end of the catheter 50, the sealing member 200 provides a seal within the butt joint, and may expand upon exposure to moisture to compensate for and seal any irregularities in the proximal end of the catheter 50. For example, if the lumens 204A, 204B at the proximal end of the catheter 50 do not fully engage the hub extensions 22, 24, the sealing member 200 may expand into those points of poor engagement to provide a seal.

Figure 5:
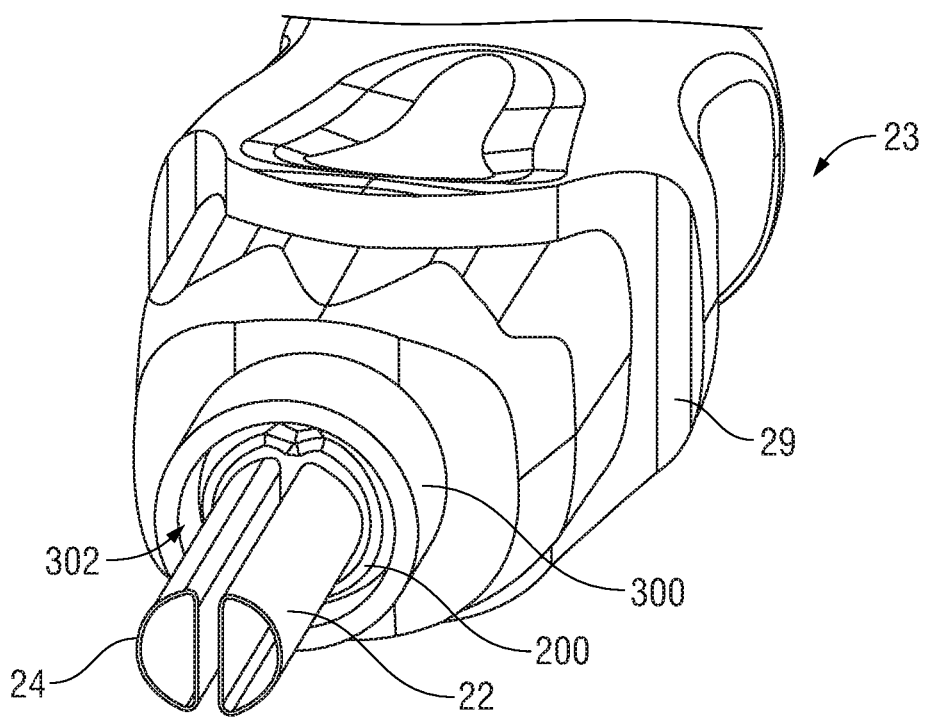
FIG. 5 is an enlarged perspective view of a distal portion of another embodiment of the present disclosure.

As illustrated in FIG. 5, another embodiment of a hub assembly, shown generally as 23, includes a hub 29. The hub 29 has a casing 300 and one or more hub extensions 22, 24 which extend distally from the hub 29. The casing 300 defines a cavity 302 dimensioned to accommodate the sealing member 200. When the catheter 50 is secured within the casing 300, a proximal end of the catheter 50 is positioned to abut the sealing member 200 within the casing 300 such that the seal between the hub extensions 22, 24 and the one or more lumens 52 of the catheter 50 is improved. As discussed above, sealing member 200 is formed from an expandable material. In this manner, the casing 300 and the sealing member 200 provide an improved sealed connection between the catheter 50 and the hub 29. In this embodiment, the sealing member 200 provides a seal at the butt joint between the proximal end of the catheter 50 and the casing 300, similar to the seal described above. Because the sealing member 200 is disposed within the cavity 302, the sealing member is constrained in the radially outward direction. This radial constraint directs the sealing member 200 into any irregularities at the proximal end of the catheter 50 as the sealing member 200 expands, thus providing a seal.

In order to prevent undesirable biological growth, the sealing members or an internal surface of the catheter may have medicinal agents or bioactive agents impregnated and/or coated thereon.

Medicinal agents that may be incorporated into or provided on the disclosed sealing members or on an internal surface of the catheter include antimicrobial agents, anti-virals, anti-fungals, and the like. Antimicrobial agents as used herein is defined by an agent which by itself or through assisting the body (immune system) helps the body destroy or resist microorganisms which may be pathogenic (disease causing). The term "antimicrobial agent" includes antibiotics, quorum sensing blockers, surfactants, metal ions, antimicrobial proteins and peptides, antimicrobial polysaccharides, antiseptics, disinfectants, anti-virals, anti-fungals, and combinations thereof.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A catheter assembly, comprising:
   a catheter, an inner wall of the catheter defining at least one lumen;
   a hub including a hub extension dimensioned to be received within the lumen of the catheter and a casing defining a cavity; and
   an expandable sealing member positioned within the cavity, the expandable sealing member configured to increase in volume upon exposure to moisture,
   wherein when the hub extension is received within the lumen of the catheter, a proximal end of the catheter abuts the expandable sealing member positioned between the inner wall of the catheter and the hub extension such that upon exposure to moisture, the expandable sealing member fills in any gaps between the hub extension and the inner wall of the catheter defining the lumen.

2. The catheter assembly of claim 1, wherein the sealing member is constrained in a radially outward direction by the casing.

3. The catheter assembly of claim 1, wherein at least a portion of at least one of the catheter or the hub includes a rigid material and wherein at least another portion of at least one of the catheter or the hub includes an elastomeric material.

4. The catheter assembly of claim 1, wherein the expandable sealing member includes at least one of a hydrophilic polymer or a hydrophilic gel.

5. The catheter assembly of claim 1, wherein the sealing member includes a bioactive agent.

6. The catheter assembly of claim 1, wherein when the hub extension is received within the lumen of the catheter, the hub extension does not fully engage the inner wall of the catheter such that one or more points of poor engagement exist between the hub extension and the inner wall, and wherein the sealing member is configured to expand into the one or more points of poor engagement between the hub extension and the inner wall of the catheter.

7. The catheter assembly of claim 1, wherein the expandable sealing member is coated or chemically bonded to at least a portion of the inner wall of the catheter defining the lumen, coated or chemically bonded to an external surface of the hub extension, or both coated or chemically bonded to the at least the portion of the inner wall of the catheter defining the lumen and the external surface of the hub extension.

8. A catheter assembly comprising:
   a catheter comprising an inner wall, a first connector surface of the inner wall defining a lumen;
   a hub including a hub extension dimensioned to be received within the lumen of the catheter, the hub extension defining a second connector surface; and
   an expandable sealing member configured to increase in volume upon exposure to moisture, wherein when the hub extension is received within the lumen of the catheter, the sealing member is configured to simultaneously contact the first connector surface and the second connector surface upon exposure to moisture.

9. The catheter assembly of claim 8, wherein at least a portion of at least one of the catheter or the hub includes a rigid material and wherein at least another portion of at least one of the catheter or the hub includes an elastomeric material.

10. The catheter assembly of claim 8, wherein the expandable sealing member includes at least one of a hydrophilic polymer or a hydrophilic gel.

11. The catheter assembly of claim 8, wherein the sealing member defines a sleeve, the sleeve being positionable on at least a portion of at least one of the first or second connector surfaces.

12. The catheter assembly of claim 11, wherein the catheter defines at least two lumens and the sleeve defines at least two lumens, each lumen of the sleeve being dimensioned to accommodate a respective lumen of the at least two lumens of the catheter.

13. The catheter assembly of claim 8, wherein the sealing member includes a bioactive agent.

14. The catheter assembly of claim 8, wherein when the hub extension is received within the lumen of the catheter, the second connector surface of the hub extension does not fully engage the first connector surface of the catheter such that one or more points of poor engagement exist between the first connector surface and the second connector surface, and wherein the sealing member is configured to expand into the one or more points of poor engagement between the first connector surface and the second connector surface.

15. The catheter assembly of claim 8, wherein when the hub extension is received within the lumen of the catheter, the sealing member is compressed between the hub and a proximal end of the catheter.

16. A catheter assembly, comprising:
   a catheter comprising an inner wall defining a lumen;
   a hub including a hub extension dimensioned to be received within the lumen of the catheter; and
   an expandable sealing member configured to increase in volume upon exposure to moisture, wherein the sealing member is coated or chemically bonded to at least a portion of the inner wall of the catheter defining the lumen, coated or chemically bonded to an external surface of the hub extension, or both coated or chemically bonded to the at least the portion of the inner wall of the catheter defining the lumen and the external surface of the hub extension,
   wherein, upon exposure to moisture and when the external surface of the hub extension is received within the lumen of the catheter, the sealing member is configured to expand to form a seal between the catheter and the hub.

17. The catheter assembly of claim 16, wherein the expandable sealing member includes at least one of a hydrophilic polymer or a hydrophilic gel.

18. The catheter assembly of claim 16, wherein the hub extension defines a first connector surface and the inner wall of the catheter defines a second connector surface defining the lumen, and wherein the sealing member defines a sleeve, the sleeve being positionable on at least a portion of at least one of the first connection surface or the second connection surface.

19. The catheter assembly of claim 16, wherein when the hub extension is received within the lumen of the catheter, the hub extension does not fully engage a surface of the catheter defining the lumen such that one or more points of poor engagement exist between the hub extension and the surface, and wherein the sealing member is configured to expand into the one or more points of poor engagement between the hub extension and the surface of the catheter.

20. The catheter assembly of claim 16, wherein when the hub extension is received within the lumen of the catheter, the sealing member is compressed between the hub and the proximal end of the catheter.

\* \* \* \* \*